United States Patent
Gillis et al.

(10) Patent No.: US 9,488,637 B2
(45) Date of Patent: Nov. 8, 2016

(54) COMBINATION OF SINGLE-CELL ELECTROPORATION AND ELECTRICAL RECORDING USING THE SAME ELECTRODE

(75) Inventors: Kevin Gillis, Columbia, MO (US); Jaya Ghosh, Columbia, MO (US)

(73) Assignee: THE CURATORS OF THE UNIVERSITY OF MISSOURI, Columbia, MO (US)

( * ) Notice: Subject to any disclaimer, the term of this patent is extended or adjusted under 35 U.S.C. 154(b) by 302 days.

(21) Appl. No.: 13/359,408

(22) Filed: Jan. 26, 2012

(65) Prior Publication Data
US 2012/0190583 A1 Jul. 26, 2012

Related U.S. Application Data

(60) Provisional application No. 61/461,988, filed on Jan. 26, 2011.

(51) Int. Cl.
| | |
|---|---|
| G01N 33/487 | (2006.01) |
| C12N 13/00 | (2006.01) |
| G01N 33/483 | (2006.01) |
| A61N 1/32 | (2006.01) |
| C12M 1/00 | (2006.01) |

(52) U.S. Cl.
CPC ......... *G01N 33/48728* (2013.01); *C12N 13/00* (2013.01); *A61N 1/327* (2013.01); *C12M 47/06* (2013.01); *G01N 33/487* (2013.01); *G01N 33/4836* (2013.01); *G01N 33/48707* (2013.01); *G01N 33/48735* (2013.01)

(58) Field of Classification Search
None
See application file for complete search history.

(56) References Cited

U.S. PATENT DOCUMENTS

| | | | |
|---|---|---|---|
| 7,456,012 B2 | 11/2008 | Ryttsen et al. | |
| 8,232,074 B2 * | 7/2012 | Jardemark et al. | 435/29 |
| 2006/0003310 A1 * | 1/2006 | Klauke | G01N 33/48728 435/4 |
| 2010/0129856 A1 | 5/2010 | Fang et al. | |

FOREIGN PATENT DOCUMENTS

| | | | | |
|---|---|---|---|---|
| WO | WO 2009073121 A1 * | 6/2009 | | G01N 33/48728 |
| WO | WO 2010027446 A2 * | 3/2010 | | G01N 33/5058 |

OTHER PUBLICATIONS

Dittami and Rabbitt, "Electrically Evoking and Electrochemically Resolving Quantal Release on a Microchip", Lab Chip, 2010, 10, p. 30-35 (First published as an Advance Article on the web Sep. 17, 2009).*

Vasanelli et al., "Space and time-resolved gene expression experiments on cultured mammalian cells by a single-cell electroporation microarray", New Biotechnology, vol. 25, No. 1, Jun. 2008.*
Fox et al., "Electroporation of Cells in Microfluidic Devices: A Review", Analytical and Bioanalytical Chemistry, 385: 474-485, 2006.*
Barizuddin, "Self-aligned Microchip Device for Automated Measurement of Quantal Exocytosis", Dissertation, University of Missouri-Columbia (May 2010).*
Barbour et al., "Combining Loose Cell-Attached Stimulation and Recording", Journal of Neuroscience Methods, 2000, pp. 199-208, vol. 103.
Cahill et al., "Simultaneous Amperometric Measurement of Ascorbate and Catecholamine Secretion from Individual Bovine Adrenal Medullary Cells", Analytical Chemistry, Aug. 1, 1995, pp. 2599-2605, vol. 67, No. 15.
Chen et al., "Amperometric Detection of Quantal Catecholamine Secretion from Individual Cells on Micromachined Silicon Chips", Analytical Chemistry, Feb. 1, 2003, pp. 518-524, vol. 75, No. 3.
Chen et al., "Controlled On-chip Stimulation of Quantal Catecholamine Release from Chromaffin Cells Using Photolysis of Caged Ca2+ on Transparent Indium-Tin-Oxide Microchip Electrodes", National Institutes of Health Public Access, 2008, pp. 1-16.
Cheng, "Monitoring Single Heart Cell Biology using Lab-on-a-Chip Technologies", A Thesis Submitted for the Degree of Doctor of Philosophy at the University of Glasgow, Mar. 2009, pp. 1-173.
Chow et al., "Delay in Vesicle Fusion Revealed by Electrochemical Monitoring of Single Secretory Events in Adrenal Chromaffin Cells", Nature, Mar. 5, 1992, pp. 60-63, vol. 365.
Elhamdani et al., "Quantal Size is Dependent on Stimulation Frequency and Calcium Entry in Calf Chromaffin Cells", Neuron, Sep. 13, 2001, pp. 819-830, vol. 31.
Fromherz et al., "Silicon-Neuron Junction: Capacitive Stimulation of an Individual Neuron on a Silicon Chip", Physical Review Letters, Aug. 21, 1995, pp. 1670-1673, vol. 75, No. 8.
Hai et al., "Long-Term, Multisite, Parallel, In-Cell Recording and Stimulation by an Array of Extracellular Microelectrodes", Journal of Neurophysiology, Jul. 2010, pp. 559-568, vol. 104.
Hay et al., "Resolution of Regulated Secretion into Sequential MgATP-dependent and Calcium-dependent Stages Mediated by Distinct Cytosolic Proteins", The Journal of Cell Biology, Oct. 1992, pp. 139-151, vol. 119, No. 1.
Lambie et al., "Experimentally Determining the IR Drop in Solution at Carbon Fiber Microelectrodes with Current Interruption and Application to Single-Cell Electroporation", National Institues of Health Public Access, 2008, pp. 1-21.

(Continued)

*Primary Examiner* — Renee Claytor
*Assistant Examiner* — Susan E Fernandez
(74) *Attorney, Agent, or Firm* — Thompson Coburn LLP; Charles Romano (57) ABSTRACT

Methods for stimulating exocytosis from a cell are provided where the same electrochemical microelectrode is used to electroporate an adjacent cell and then measure quantal exocytosis from the adjacent cell. Also provided are methods for stimulating and measuring exocytosis from a select cell population arrayed on a chip comprising addressable electrodes. Calcium independent stimulation of exocytosis with inorganic anions such as chloride ions is also provided. These methods can provide for specific stimulation of a desired subset of cells without exposing other nearby cells to the stimulus.

8 Claims, 8 Drawing Sheets

(56) References Cited

OTHER PUBLICATIONS

Liu et al., "A Microwell Device for Targeting Single Cells to Electrochemical Microelectrodes for High-throughput Amperometric Detection of Quantal Exocytosis", National Institutes of Health Public Access, 2012, pp. 1-16.
Olofsson et al., "Single-Cell Electroporation", Current Opinion in Biotechnology, 2003, pp. 29-34, vol. 14.
Plattner et al., "Ultrastructural Organization of Bovine Chromaffin Cell Cortex-Analysis by Cryofixation and Morphometry of Aspects Pertinent to Exocytosis", The Journal of Cell Biology, Dec. 1997, pp. 1709-1717, vol. 139, No. 7.
Ryttsen et al., "Characterization of Single-Cell Electroporation by Using Patch-Clamp and Fluorescence Microscopy", Biophysical Journal, Oct. 2000, pp. 1993-2001, vol./No. 79(4).
Segura et al., "Automatic Analysis for Amperometrical Recordings of Exocytosis", Journal of Neuroscience Methods, 2000, pp. 151-156, vol. 103.
Spegel et al., "Fully Automated Microchip System for the Detection of Quantal Exocytosis From Single and Small Ensembles of Cells", Lab Chip, 2008, pp. 323-329, vol. 8.
Spegel et al., "On-Chip Determination of Dopamine Exocytosis Using Mercaptopropionic Acid Modified Microelectrodes", Electroanalysis, 2007, pp. 263-271, vol. 19, No. 2-3.
Sun et al., "On-Chip Amperometric Measurement of Quantal Catecholamine Release Using Transparent Indium Tin Oxide Electrodes", Analytical Chemistry, Apr. 15, 2006, pp. 2521-2525, vol. 78, No. 8.
Wang et al., "Single-Cell Electroporation", Analytical and Bioanalytical Chemistry, 2010, pp. 3235-3248, vol. 397.
Wegener et al., "Recovery of Adherent Cells after In Situ Electroporation Monitored Electrically", BioTechniques, Aug. 2002, pp. 348-357, vol. 33, No. 2.
Wightman et al., "Temporally Resolved Catecholamine Spikes Correspond to Single Vesicle Release From Individual Chromaffin Cells", Proceedings of the National Academy of Sciences, USA, Dec. 1991, pp. 10754-10758, vol. 88.
Yang et al., "Phosphomimetic Mutation of Ser-187 of SNAP-25 Increases both Syntaxin Binding and Highly CA2+-sensistive Exocytosis", Journal of General Physiology, Mar. 2007, pp. 233-244, vol. 129, No. 3.
Zeck et al., "Noninvasive Neuroelectronic Interfacing With Synaptically Connected Snail Neurons Immobilized on a Semiconductor Chip", Proceedings of the National Academy of Sciences, Aug. 28, 2001, pp. 10457-10462, vol. 98, No. 18.
Amatore et al., "Coupling of Electrochemistry and Fluorescence Microscopy at Indium Tin Oxide Microelectrodes for the Analysis of Single Exocytotic Events", Angewandte Chemie—International Edition, 2006, pp. 4000-4003, vol. 45.
Amatore et al., "Relationship Between Amperometric Pre-Spike Feet and Secretion Granule Composition in Chromaffin Cells: An Overview", Biophysical Chemistry, 2007, pp. 181-189, vol. 129.
Bard et al., Electrochemical Methods: Fundamentals and Applications, 2001, Wiley & Sons, New York.
Barizuddin et al., "Automated Targeting of Cells to Electrochemical Electrodes Using a Surface Chemistry Approach for the Measurement of Quantal Exocytosis", ACS Chemical Neuroscience, 2010, pp. 590-597, vol. 1.
Berberian et al., "Improved Surface-Patterned Platinum Microelectrodes for the Study of Exocytotic Events", Analytical Chemistry, 2009, pp. 8734-8740, vol. 81.
Dias et al., "An Electrochemical Detector Array to Study Cell Biology on the Nanoscale", Nanotechnology, 2002, pp. 285-289, vol. 13.
Fiaccabrino et al., "Array of Individually Addressable Microelectrodes", Sensors and Actuators: B. Chemical, 1994, pp. 675-677, vol. 19.
Gao et al., "A Microfluidic Cell Trap Device for Automated Measurement of Quantal Catecholamine Release from Cells", Lab on a Chip—Miniaturisation for Chemistry and Biology, 2009, pp. 3442-3446, vol. 9.
Gao et al., "Magnetron Sputtered Diamond-Like Carbon Microelectrodes for On-Chip Measurement of Quantal Catecholamine Release from Cells", Biomedical Microdevices, 2008, pp. 623-629, vol. 10.
Hafez et al., "Electrochemical Imaging of Fusion Pore Openings by Electrochemical Detector Arrays", Proceedings of the National Academy of Sciences of the United States of America, 2005, pp. 13879-13884, vol. 102.
Hochstetler et al., "Real-Time Amperometric Measurements of Zeptomole Quantities of Dopamine Released from Neurons", Analytical Chemistry, 2000, pp. 489-496, vol. 72.
Ino et al., "Addressable Electrode Array Device with IDA Electrodes for High-Throughput Detection", Lab on a Chip—Miniaturisation for Chemistry and Biology, 2011, pp. 385-388, vol. 11.
Long et al., "Noise at Microelectrodes and Microelectrode Arrays in Amperometry and Voltammetry", Analytical Chemistry, 1988, pp. 2309-2311, vol. 60, No. 20.
Neher et al., "Electrophysiological and Electrochemical Techniques for Studying Control Mechanisms of Secretion in Neuroendocrine Cells", Bioelectrochemistry and Bioenergetics, 1995, pp. 251-253, vol. 38.
Pei et al., "Individually Addressable Gel-Integrated Voltammetric Microelectrode Array for High-Resolution Measurement of Concentration Profiles at Interfaces", Analytical Chemistry, 2001, pp. 2273-2281, vol. 73.
Sen et al., "Preferential Cell Attachment to Nitrogen-Dopes Diamond-Like Carbon (DLC:N) for the Measurement of Quantal Exocytosis", Biomaterials, 2009, pp. 1604-1612, vol. 30, No. 8.
Shin, "Nano- and Micro- Scale Studies of Exocytosis", A Dissertation presented to the Faculty of the Graduate School University of Missouri-Columbia, May 2007, pp. 1-119.
Yao et al., "A high-throughput electrochemical microelectrode array for amperometric measurement", Abstract, World Congress on Bioengineering, WACBE World Association for Chinese Biomedical Engineers, Aug. 18-21, 2011, www.wacbe.org.
Yao et al., "A Low Noise Electrochemical Microelectrode Array for Measurement of Cell Secretion", Poster presented at the 5th World Congress on Bioengineering 2011, Taiwan, Taiwan, Dalton Cardiovascular Research Center, Department of Biological Engineering, Department of Pharmacology and Physiology, University of Missouri, Columbia, 6 Pages.
Yao et al., "Quantification of Noise Sources for Amperometric Measurement of Quantal Exocytosis Using Microelectrodes", Analyst, 2012, pp. 2674-2681, vol. 137.
Yao et al.,"A Multiplexed Electrochemical Electrode Array for High Throughput Measurements of Quantal Exocytosis", Biophysical Journal, Feb. 2011, pp. 607a, vol. 100, Issue 3, Supplement 1.
Yao et al.,"A Multiplexed Electrochemical Electrode Array for High Throughput Measurements of Quantal Exocytosis", Poster presented at the Biophysical Society annual meeting, Mar. 5-9, 2011, Baltimore, MD, www.biophysics.org.
Yao et al.,"A Novel Multiplexing Approach for Individually Addressable Electrode Arrays with Reduced External Connections", Abstract, Biomedical Engineering Society, Oct. 12-15, 2011, Hartford, CT, www.bmes.org.
Yao et al.,"A Novel Multiplexing Approach for Individually Addressable Electrode Arrays with Reduced External Connections", Poster presented at the Biomedical Engineering Society annual meeting, Oct. 12-15, 2011, Hartford, CT, www.bmes.org.
Zor et al., "Real-Time Monitoring of Cellular Dynamics Using a Microfluidic Cell Culture System with Integrated Electrode Array and Potentiostat", 15th International Conference on Miniatured Systems for Chemistry and Life Sciences, Oct. 2-6, 2011, Seattle, Washington, USA, pp. 1532-1535.

* cited by examiner

COMBINATION OF SINGLE-CELL ELECTROPORATION AND ELECTRICAL RECORDING USING THE SAME ELECTRODE

CROSS-REFERENCE TO RELATED APPLICATIONS

This patent application claims the benefit of U.S. Provisional Patent Application No. 61/461,988, filed Jan. 26, 2011, and incorporated herein by reference in its entirety.

STATEMENT REGARDING GOVERNMENT SUPPORT

This invention was made with Government support under contract number NS048826 awarded by the National Institutes of Health. The Government has certain rights in the invention.

FIELD OF INVENTION

The present invention relates to a microchip device for measurements of substances released from a cell, more specifically, to a microchip device capable of electropermeabilizing a cell membrane and measurement of release of electrochemically active substances from the cell using the same electrode.

SUMMARY OF INVENTION

The present invention provides a new and improved technology allowing simultaneous electrochemical detection and cell stimulation. The invention develops the on-chip methods for stimulating exocytosis from select cell population on the chip and uses the same electrode to electrically stimulate the adjacent cell and subsequently measure the release of electrochemically active substances.

The invention further provides a new and improved microfabricated device containing arrays of electrochemical electrodes with one possible application being to increase the throughput of single-cell measurements of quantal exocytosis from neuroendocrine cells. According to one embodiment of the invention, voltage pulses may be applied to planar electrodes to promote efficient cell electropermeabilization to trigger exocytosis upon $Ca^{+2}$ influx from $Ca^{+2}$-buffered bath solutions. In certain embodiments, voltage pulses may be applied to planar electrodes to promote efficient cell electropermeabilization to trigger exocytosis upon influx of other stimulatory substances. The amplifier may be modified to allow it to transiently pass large currents to enable electroporation, yet record pA amperometric currents with low noise.

Methods for stimulating and measuring exocytosis from a select cell population are provided. In certain embodiments, methods for stimulating and measuring exocytosis from a select cell population can comprise, for a select population of cells arrayed on a chip comprising addressable electrodes, electrically stimulating the select cell population with the electrodes, and measuring release of electrochemically active substances from the select cell population, wherein a single electrode is used to stimulate a cell adjacent to the electrode surface and to measure release of electrochemically active substances from the adjacent cell are provided. In certain embodiments of any of the aforementioned methods, the methods can further comprise arraying a plurality of cells on the chip. In certain embodiments of any of the aforementioned methods, the select cell population comprises cells adjacent to surfaces of essentially all of the addressable electrodes. In certain embodiments of any of the aforementioned methods, the select cell population comprises a subset of cells that are adjacent to surfaces of a subset of the electrodes. In certain embodiments of any of the aforementioned methods, the stimulation comprises triggering an action potential in the select cell population with a transient electric field. In certain embodiments of any of the aforementioned methods, the stimulation comprises electroporating the select cell population. In certain embodiments of any of the aforementioned methods, a membrane-impermeable substance is introduced into the select cell population by electroporation. In certain embodiments of any of the aforementioned methods, the membrane-impermeable substance comprises a peptide, an antibody, a DNA molecule, or an RNA molecule. In certain embodiments of any of the aforementioned methods, DNA molecule or the RNA molecule is used to express a gene of interest or to inhibit expression of a gene of interest in the select cell population. In certain embodiments of any of the aforementioned methods, the select cell population is incubated after the stimulation and then measured. In certain embodiments of any of the aforementioned methods, an agent is applied after the stimulation of the subset of cells. In certain embodiments of any of the aforementioned methods, the electrode is comprised of gold, indium tin oxide, diamond-like carbon, or combinations thereof. In certain embodiments of any of the aforementioned methods, the cell adjacent to the electrode surface is either: i) within less than about 3 micrometers, about 2 micrometers, about 1 micrometers, or about 0.5 micrometers of the electrode surface; or, ii) is contacting the electrode surface.

Also provided herein are methods for stimulating and measuring exocytosis from a cell. In certain embodiments, the methods for stimulating and measuring exocytosis from a cell can comprise: applying, through an electrode, a voltage to a cell that is adjacent to a surface of the electrode, the applied voltage being sufficient to cause a stimulation of the cell; and recording, through the same electrode, a current signal indicative of a release of an electrochemically active substance from the stimulated cell. In certain embodiments of any of these aforementioned methods, the applied voltage comprises a voltage pulse. In certain embodiments of any of these aforementioned methods, the recording step is performed while the cell remains adjacent the electrode. In certain embodiments of any of these aforementioned methods, the applied voltage pulse comprises a first pulse portion and a second pulse portion, wherein the first pulse portion causes the cell stimulation, and wherein the recording step is performed during the second pulse portion. In certain embodiments of any of these aforementioned methods, the applied voltage pulse comprises a series of the voltage pulses, and the recording step is performed during a plurality of the second pulse portions for the series. In certain embodiments of any of these aforementioned methods, the recording step is performed within one second of the applying step. In certain embodiments of any of these aforementioned methods, the current signal comprises an amperometric spike. In certain embodiments of any of these aforementioned methods, the current signal is not a slowly changing background Faradaic current. In certain embodiments of any of these aforementioned methods, the stimulation comprises a triggering of an action potential in the cell. In certain embodiments of any of these aforementioned methods, the stimulation comprises electroporation of the cell. In certain embodiments of any of these aforementioned methods, a membrane-impermeable substance is introduced into the cell by electroporation. In certain embodiments of any of these aforementioned methods, the membrane-impermeable substance introduced by electroporation comprises a peptide, an antibody, a DNA molecule, or an RNA molecule. In certain embodiments of any of these aforementioned methods, the methods can comprise performing the applying step and the recording step for a plurality of cells that are adjacent to a plurality of the electrodes, the electrodes being part of a microchip electrode array, and wherein the applying step comprises selectively addressing the electrodes with the voltage pulses to stimulate a desired subset of the cells without exposing other nearby cells to stimulation. In certain embodiments of any of these aforementioned methods, the electrode comprises an electro-chemical electrode. In certain embodiments of any of these aforementioned methods, the electro-chemical electrode is comprised of gold, indium tin oxide, diamond-like carbon, or combinations thereof. In certain embodiments of any of these aforementioned methods, the cell is a neuroendocrine cell and quantal exocytosis from the cell is recorded. In certain embodiments of any of these aforementioned methods, the adjacent cell is contacting the electrode surface or within about 3 micrometers of the electrode surface.

Also provided are methods for stimulating with exogenous inorganic anions and measuring exocytosis from a cell that results from this stimulation. In certain embodiments, the methods for stimulating and measuring exocytosis from a cell can comprise: applying, through an electrode, a voltage to a cell that is adjacent to a surface of the electrode in the presence of an exogenous inorganic anion, the applied voltage and concentration of the inorganic anion being sufficient to cause a stimulation of the cell; and, recording, through the same electrode, a current signal indicative of a release of an electrochemically active substance from the stimulated cell. In certain embodiments of any of these aforementioned methods, the applied voltage comprises a voltage pulse. In certain embodiments of any of these aforementioned methods, the recording step is performed while the cell remains adjacent the electrode. In certain embodiments of any of these aforementioned methods, the applied voltage pulse comprises a first pulse portion and a second pulse portion, wherein the first pulse portion causes the cell stimulation, and wherein the recording step is performed during the second pulse portion. In certain embodiments of any of these aforementioned methods, the applied voltage pulse comprises a series of the voltage pulses, and the recording step is performed during a plurality of the second pulse portions for the series. In certain embodiments of any of these aforementioned methods, the exogenous chloride ion is at a concentration of at least about 10 millimolar. In certain embodiments of any of these aforementioned methods, the exogenous inorganic anion is at a concentration of at least about 10 millimolar or at least about 15 millimolar to any one of about 50 millimolar, about 75 millimolar, about 100 millimolar, about 125 millimolar, about 150 millimolar, about 175 millimolar, or about 200 millimolar. In certain embodiments of any of these aforementioned methods, exogenous calcium ions are essentially absent when the voltage pulse is applied. In certain embodiments of any of these aforementioned methods, the recording step is performed while the cell remains adjacent the electrode. In certain embodiments of any of these aforementioned methods, the applied voltage pulse comprises a first pulse portion and a second pulse portion, wherein the first pulse portion causes the cell stimulation, and wherein the recording step is performed during the second pulse portion.

In certain embodiments of any of these aforementioned methods, the recording step is performed within one second of the applying step. In certain embodiments of any of these aforementioned methods, the current signal comprises an amperometric spike. In certain embodiments of any of these aforementioned methods, the current signal is not a slowly changing background Faradaic current. In certain embodiments of any of these aforementioned methods, the methods can comprise performing the applying step and the recording step for a plurality of cells that are adjacent to a plurality of the electrodes, the electrodes being part of a microchip electrode array, and wherein the applying step comprises selectively addressing the electrodes with the voltage pulses to stimulate a desired subset of the cells without exposing other nearby cells to stimulation. In certain embodiments of any of these aforementioned methods, the electrode comprises an electro-chemical electrode. In certain embodiments of any of these aforementioned methods, the electro-chemical electrode is comprised of gold, indium tin oxide, diamond-like carbon, or combinations thereof. In certain embodiments of any of these aforementioned methods, the cell is a neuroendocrine cell and quantal exocytosis from the cell is recorded. In certain embodiments of any of these aforementioned methods, the adjacent cell is contacting the electrode surface or within about 3 micrometers of the electrode surface. In certain embodiments of any of these aforementioned methods, the inorganic anion is selected from the group consisting of bromide, chloride, iodide, and sulfate. In certain embodiments of any of these aforementioned methods, the inorganic anion is a chloride ion.

DESCRIPTION OF DRAWINGS

FIG. 1 is the schematic illustration of electroporation. The two basic steps of the approach are shown here. Left: Voltage pulse applied to cell sitting on the electrode (acting as stimulating electrode in this case). Right: Pores form on the plasma membrane i.e. the cell is electropermeabilized. $Ca^{2+}$ or other stimulating substances in the bath solution flow into the cell and evoke exocytosis. Resulting amperometric spikes are recorded using the same electrode (now acting as the recording electrochemical electrode).

FIG. 2. Electroporation leads to exocytosis. Electrical impulse was given at time indicated by arrow. Left: $[Ca^{2+}]$ in bath was buffered to ~4 µM with HEDTA and $[Cl^-]$ was ~18 mM. Pulse was to +6V for 0.1 ms (train of 7 pulses). Right: $[Ca^{2+}]$ in bath was 2 mM and $[Cl^-]$ was ~160 mM. Pulse was to +6V for 0.1 ms (train of 7 pulses).

FIGS. 3A and 3B. Electrical stimulation leads to electroporation as demonstrated by dye uptake and exocytosis as measured by the underlying electrochemical electrode. A. Fluorescent images demonstrating propidium iodide staining of chromaffin cell before (left) and after (right) applying a stimulus consisting of a train of 7, 0.1 ms pulses to 6V. Right: Amperometric current including spikes indicating exocytosis from the underlying DLC electrode in response to the electrical stimulus (arrow). B. Images demonstrating trypan blue staining of chromaffin cell before (above) and after (below) applying a stimulus consisting of a train of 7, 0.1 ms pulses to 6 V. Right: Amperometric current including spikes indicating exocytosis from the underlying gold electrode in response to the electrical stimulus (arrow).

FIG. 5. Electrochemical measurement of electropermeabilization-induced exocytosis on a chip. Representative amperometric spikes recorded from a single cell on a gold (Au) microelectrode in response to electropermeabilization. The stimulus consisted of a train of 7, 0.1 ms pulses to 6 V. The bath solution contained 135 mM NaCl and 2 mM $CaCl_2$.

FIG. 6. Electropermeabilization-induced exocytosis is sensitive to $[Cl^-]_e$. The frequency of release events from a single chromaffin cell electropermeabilized on-chip was found to vary with $[Cl^-]_e$. (a) Spike frequency reflecting the rate of exocytosis was higher in the higher-$[Cl^-]_e$ solution and (b) fell dramatically with a decrease in $[Cl^-]_e$. (c) Increasing $[Cl^-]_e$ to 32 mM led to a subsequent increase in spike frequency in the same cell.

DETAILED DESCRIPTION OF INVENTION

High-resolution assays of release of electroactive materials from cells, such as hormones, transmitter, and reactive oxygen species are needed for a number of medically related problems. The invention discussed here enables both stimulation of individual cells and measurement of cell release in a compact device.

Peptides, hormones and neurotransmitters are stored in membrane-bound vesicles within endocrine cells and neurons. Upon stimulation, a rise in intracellular $Ca^{2+}$ concentration ($[Ca^{2+}]_i$) triggers the fusion of vesicles with the plasma membrane and release of hormone or neurotransmitter to the outside of the cell in a process called exocytosis. Since fusion of each vesicle discharges a discrete packet of signaling molecules, exocytosis is inherently a quantal process. Understanding the mechanism of vesicle fusion and transmitter release is of broad medical significance. The Drug L-Dopa exerts its effect in treating Parkinson's disease by increasing the size of released quanta. Botulinum neurotoxins inhibit transmitter release via cleavage of so-called SNARE proteins at specific sites. Botulinum toxin A is, in addition to its use in cosmetic treatment, applied for the treatment of strabismus, blepharospasm, focal spasms, and cervical dystonia. Thus understanding exocytosis will not only aid in the improvement and development of therapies for diseases where release of neurotransmitters is compromised, but it will also advance our understanding of treatments that modulate transmitter release.

In order to achieve this goal, high-resolution assays of exocytosis are needed to quantify transmitter release from individual vesicles. Recently our group and others have been developing microfabricated devices containing arrays of electrochemical microelectrodes to measure the release of electroactive transmitter at the single-cell and single-vesicle level [1-5]. The goal of these efforts is to dramatically increase the throughput of single-cell measurements of transmitter release from neuroendocrine cells and to develop technology that allows simultaneous electrochemical detection and fluorescence imaging of single fusion events. This technology will enable high throughput discovery of drugs such as L-DOPA that affect quantal exocytosis and screening for toxins that inhibit neurotransmitter release.

Microchip approaches to measure exocytosis currently could benefit from specific, powerful approaches for stimulating the cells. For example, one may want to stimulate a subset of the cells, apply a drug for a certain time, stimulate a different subset of cells, wash out the drug and stimulate a third subset of cells to test for reversibility. A sample application is determining the time course of increasing quantal size by L-Dopa application and the recovery after withdrawal of the drug. Another example is when carrying out fluorescent imaging using high-power objective lenses because only a small number of cells can be imaged at once.

A common method for selective stimulation is to apply the secretagogue with an application pipette mounted on a micromanipulator. This is a slow and laborious procedure, however, and it is not always possible to specifically stimulate the desired subset of cells without exposing other nearby cells to the agent. Our invention includes electrical stimulation approaches, which allow specific, addressable stimulation down to the single-cell level, precise timing of the stimulus, and complete integration within the microchip platform.

Electrical stimulation can elicit exocytosis in at least two ways. First, triggering action potentials in excitable cells with a transient electric field is a widely used technique in neuroscience and can be implemented on microchips (e.g., [6, 7]). A second approach is to apply a strong enough electric field to permeabilize the cell membrane [8]. Electropermeabilizing the plasma membrane bypasses the normal excitation pathway mediated by membrane depolarization followed by influx of $Ca^{2+}$ through voltage-gated $Ca^{2+}$ channels. Instead, $Ca^{2+}$ or other stimulating substances enter through the permeabilized membrane. This allows one to sort out whether a drug or toxin or protein mutation affects exocytosis through a direct effect on exocytosis as opposed to an effect on the membrane potential mediated by ion channels.

In certain embodiments, electroporation-induced exocytosis that is dependent on the exogenous monovalent anion or divalent anion concentration, but not the exogenous calcium ion ($Ca^{2+}$) concentration in the bath solution, can be obtained with the methods provided herein. It is thus possible to stimulate and record exocytosis from cells in bath solutions where sufficient concentrations of exogenous monovalent anion or divalent anion are present but exogenous calcium ions are essentially absent. In certain embodiments, an exogenous monovalent anion or divalent anion at a concentration of at least about 10 millimolar, or at least about 15 millimolar is sufficient to stimulate exocytosis. In certain embodiments of any of these aforementioned methods, an exogenous monovalent anion or divalent anion concentration of at least about 10 millimolar, at least about 15 millimolar, or at least about 20 millimolar to any one of about 50 millimolar, about 75 millimolar, about 100 millimolar, about 125 millimolar, about 150 millimolar, about 175 millimolar, or about 200 millimolar is sufficient to stimulate exocytosis. In the context of certain embodiments, exogenous calcium ions can be considered to be essentially absent when the bath solution is prepared without addition of a calcium ion source compound or when the bath solution that lacks a calcium ion source compound further comprises an agent that chelates or otherwise removes free calcium ions from solution. Calcium ion source compounds include, but are not limited to, calcium chloride, calcium carbonate, calcium hydroxide, calcium nitrate, and the like. Agents that chelate calcium include, but are not limited to, ethylenediaminetetraacetic acid (EDTA) and ethylene glycol tetraacetic acid (EGTA). Monovalent anions that can be used in these methods include, but are not limited to, chloride, iodide, and bromide anions. Divalent anions that can be used in these methods include, but are not limited to, sulfate anion. In most but not all embodiments, the monovalent or divalent anion used is a small inorganic anion. The large organic ion glutamate has not been effective in stimulating exocytosis.

In certain embodiments, electroporation-induced exocytosis that is dependent on the exogenous chloride ion ($Cl^-$) concentration, but not the exogenous calcium ion ($Ca^{2+}$) concentration in the bath solution, can be obtained with the methods provided herein. It is thus possible to stimulate and record exocytosis from cells in bath solutions where sufficient concentrations of exogenous chloride ion are present but exogenous calcium ions are essentially absent. In certain embodiments, an exogenous chloride ion at a concentration of at least about 10 millimolar or at least about 15 millimolar is sufficient to stimulate exocytosis. In certain embodiments of any of these aforementioned methods, an exogenous chloride ion concentration of at least about 10 millimolar, at least about 15 millimolar, or at least about 20 millimolar to any one of about 50 millimolar, about 75 millimolar, about 100 millimolar, about 125 millimolar, about 150 millimolar, about 175 millimolar, or about 200 millimolar is sufficient to stimulate exocytosis. In the context of certain embodiments, exogenous calcium ions can be considered to be essentially absent when the bath solution is prepared without addition of a calcium ion source compound or when the bath solution that lacks a calcium ion source compound further comprises an agent that chelates or otherwise removes free calcium ions from solution. Calcium ion source compounds include, but are not limited to, calcium chloride, calcium carbonate, calcium hydroxide, calcium nitrate, and the like. Agents that chelate calcium include, but are not limited to, ethylenediaminetetraacetic acid (EDTA) and ethylene glycol tetraacetic acid (EGTA). Without seeking to be limited by theory, it is believed that electroporation may sensitize vesicles to $Cl^-$, perhaps due to an osmotic effect mediated by CLC $Cl^-$ channels or other chloride ion channels in the membranes of secretory vesicles.

Electroporation also allows one to introduce membrane-impermeable substances into the cell, such as peptides or antibodies, to modulate protein function or second-messenger cascades. DNA or RNA can also be introduced into cells via electropermeabilization in order to express or inhibit expression of a gene of interest. The terms "electroporation" and "electropermeabilization" are considered to describe the same process and are thus used interchangeably herein. Whereas devices for electropermeabilization of individual cells on microchips already exist, the novel feature of our invention is a compact way of both inducing electroporation and recording the signal which results from release of substances from the cell induced by the electroporation-induced cell perturbation. For example, electroporation of an array of single cells on a chip could be used to cause uptake of DNA. Following electroporation, the array could be returned to an incubator to allow time for expression of the protein encoded by the DNA. Following protein expression, the transfected cells would already be specifically located adjacent to the recording electrodes for experimentation to determine the effect of the expressed protein.

Measurement of Cell Exocytosis and Electropermeabilization of the Cell Using the Same Electrode.

A drawback of permeabilization approaches is that soluble cell components leak out of the cell, leading to a "rundown" of exocytosis over several minutes [9]. A desirable feature of our on-chip stimulation approach is that we can measure exocytosis immediately (<1 s) after electropermeabilization, before "rundown" occurs, because the cells are already located adjacent to the recording electrode. Another desirable feature of our on-chip approach is that we can distinguish bona-fide exocytosis (amperometric spikes) from release of cytosolic transmitter or other electroactive compounds (which result in a slowly changing background Faradaic current) [10].

A number of groups have implemented cell electroporation on a microchip, usually by applying a high electric field in a microfluidic channel or through a narrow aperture (reviewed in [11]). Recently the Orwar group has studied electroporation at the single-cell level using carbon-fiber electrodes, thus demonstrating the feasibility of electroporation using polarizable microelectrodes suitable for electrochemistry [12]. When a microelectrode passes current, the voltage in the electrolyte solution drops within a few tens of μm from the electrode surface due to the small electrode geometry and diverging electric field [12, 13]. A voltage gradient in the solution surrounding the cell leads to an altered potential across regions of the membrane that are orthogonal to the electric field lines. Electroporation results when the local transmembrane voltage exceeds ~200 mV. In our experiments the cell is of necessity directly adjacent to the electrochemical electrode. In certain embodiments, a cell is directly adjacent to the electrochemical electrode when it is within about 3 micrometers of the electrode surface. In other certain embodiments, a cell is directly adjacent to the electrochemical electrode when it is within about 2 micrometers, about 1 micrometer, or about 0.5 micrometers of the electrode surface. In still other certain embodiments, a cell is directly adjacent to the electrochemical electrode when it is in contact with the electrode surface. Therefore a transient current passed by the electrode can produce a large transient voltage gradient and permeabilization of the membrane near the electrode. Thus the electrochemical electrode is in the perfect position to also serve as an electrical stimulus electrode.

Figure 2:
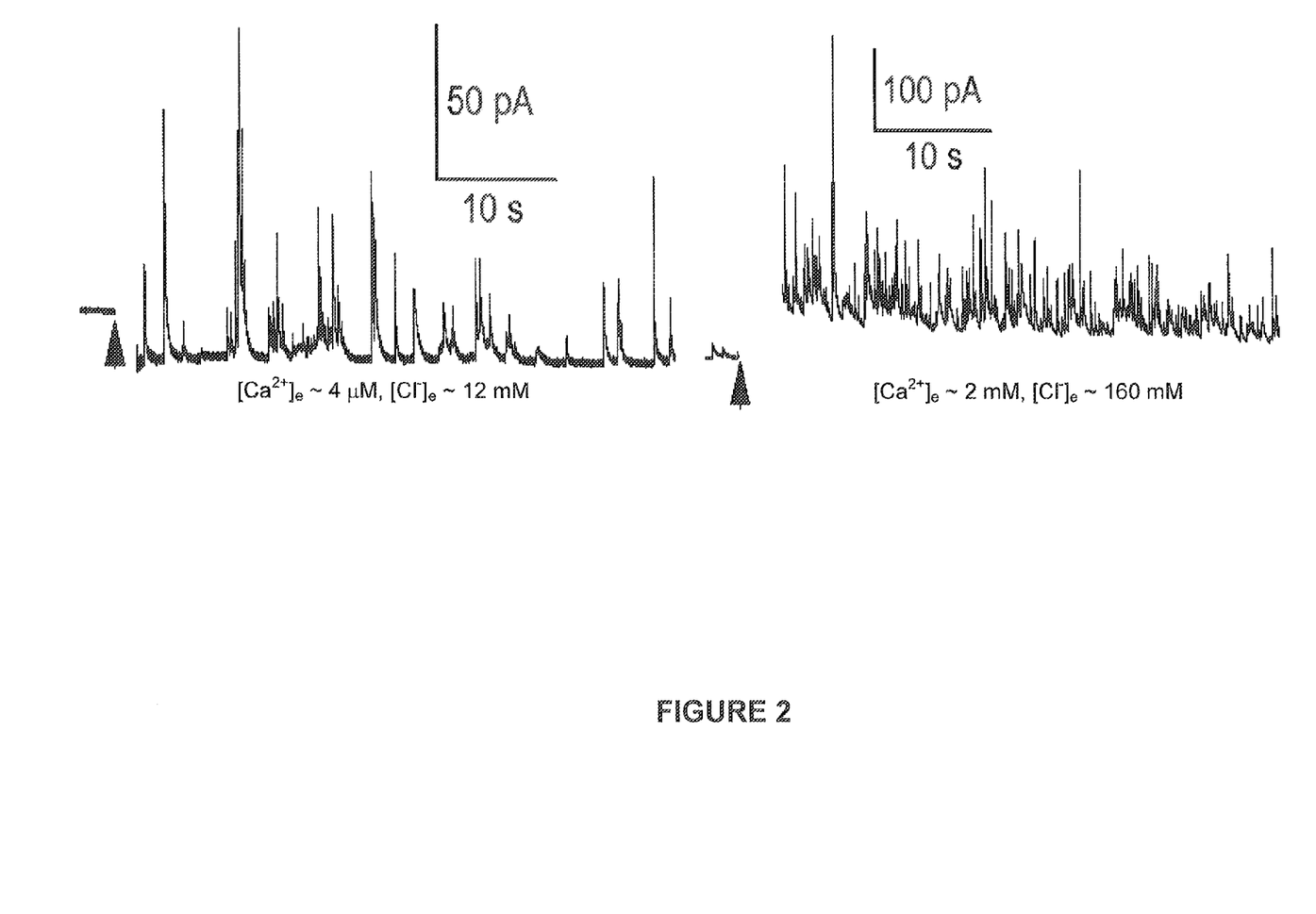

A consideration with this novel stimulus-recording electrode approach is that the dynamic range of the potentiostat be sufficient to supply a large current to induce electroporation, yet also resolve the picoamp-level currents associated with amperometric events. An example of a circuit that can be employed in this regard is described at FIG. 5 of reference [14] cited herein. In our work, we have modified a VA-10 potentiostat in collaboration with the manufacturer, NPI Inc. The modification adds a diode network in parallel with the op-amp feedback resistor, as described in FIG. 15 of reference [14]. The diodes "turn on" to bypass the feedback resistor to allow a large transient current to be supplied to the electrode in response to a voltage step. Once the capacitive current settles the diodes "turn off" to allow low-noise I-V conversion by the feedback resistor [14]. FIG. 2 presents sample recordings where we elicited exocytosis following pulses in voltage applied to the microchip working electrode (arrows). The left trace shows a typical response when the cell is bathed in a solution where the $Ca^{2+}$ concentration is buffered to ~4 μM and the $Cl^-$ concentration is ~18 mM. The right trace depicts a typical response when the bath contains 2 mM $Ca^{2+}$ and ~160 mM $Cl^-$. These results indicate that electric-pulse-induced exocytosis is dependent on the composition of the bath solution and is not a direct stimulation of exocytosis by the electric pulse. These results are not consistent with a mechanism whereby the voltage pulse leads to depolarization-induced $Ca^{2+}$ influx through $Ca^{2+}$ channels because brief membrane depolarization does not lead to exocytosis lasting for tens of seconds.

Validation of Approach: Occurrence of Electroporation.

Figure 3A:
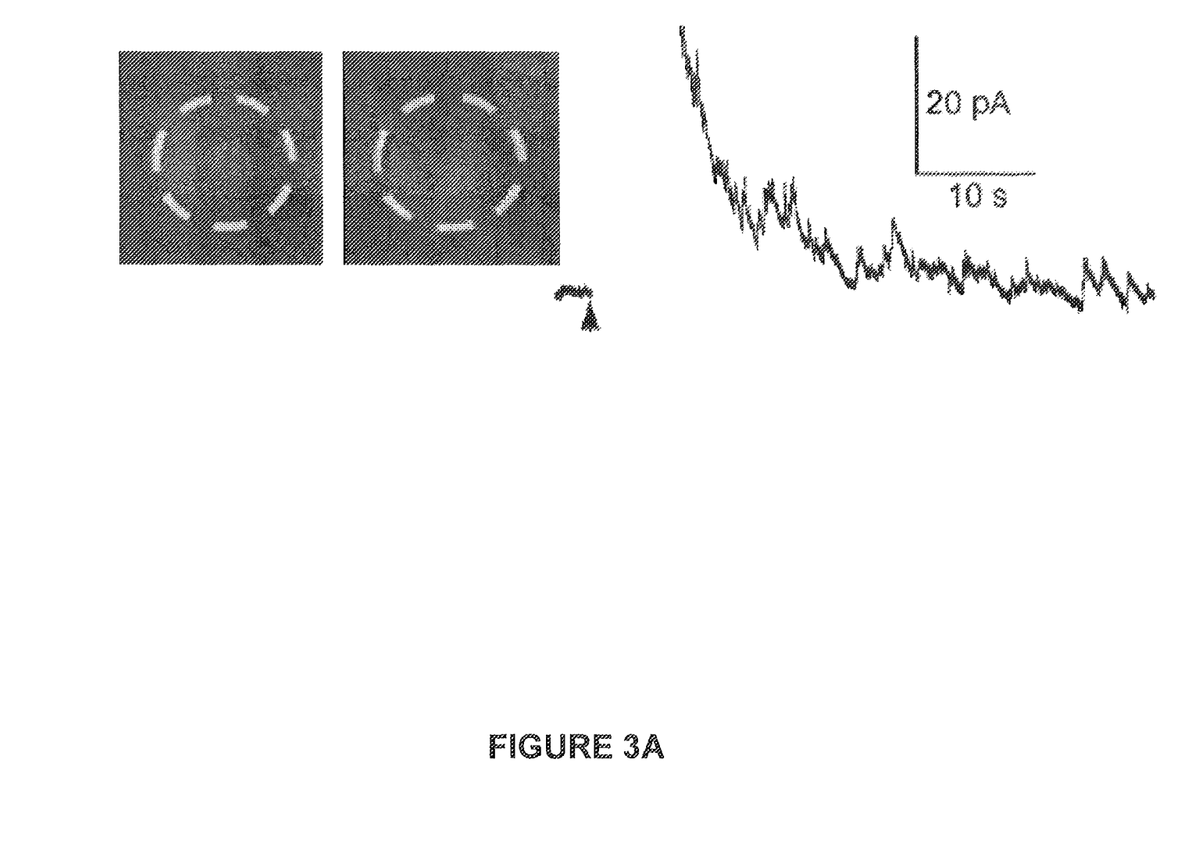
Figure 3B:
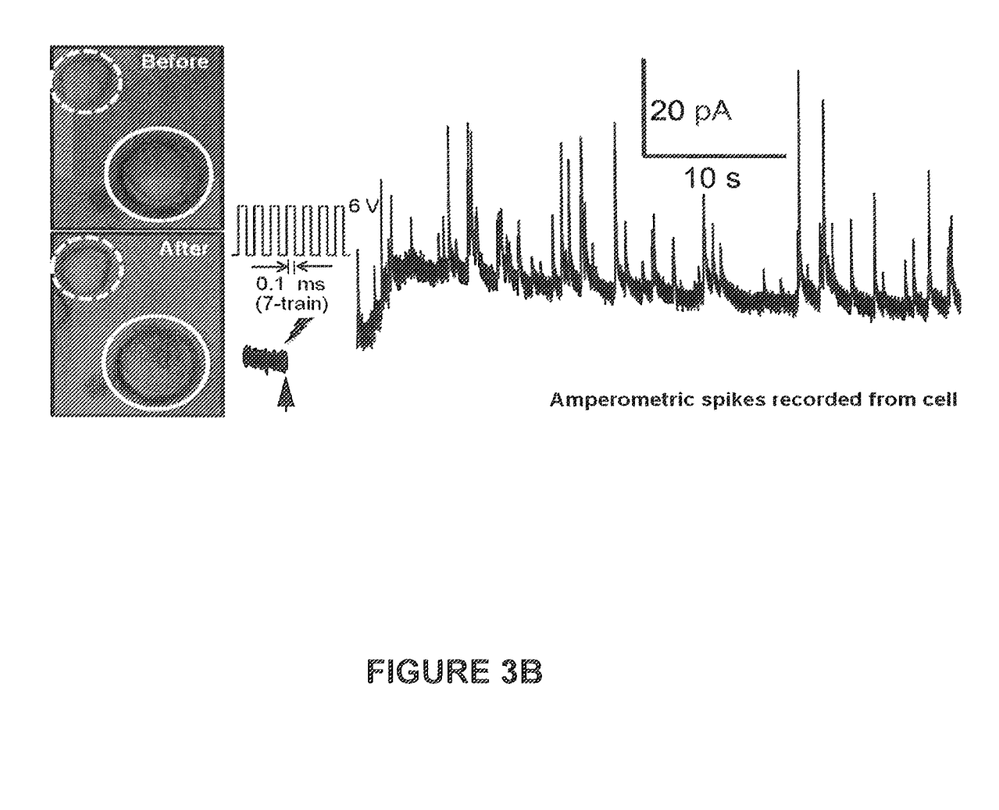

Propidium iodide is a known membrane-impermeant nucleic acid stain that is excluded from viable cells. However, the increase in membrane permeability that results from electroporation allows the dye to enter the cell. Once it enters the cell, the dye binds to the nucleic acids and its fluorescence is enhanced 20- to 30-fold. Propidium iodide staining indicates that the cell has become receptive to entry of exogenous molecules that would otherwise be excluded (FIG. 3A). Trypan Blue is another known membrane-impermeant nucleic acid stain that is excluded from viable cells. The increase in membrane permeability that results from electroporation also allows the Trypan Blue dye to enter the cell. Once it enters the cell, the Trypan Blue dye binds to the nucleic acids. Trypan blue staining indicates that the electroporated cell has become receptive to entry of exogenous, membrane impermeable trypan blue molecules that would have been excluded in the absence of electroporation (FIG. 3B).

Further evidence for electroporation is that large voltage pulses lead to a precipitous drop in membrane resistance in our patch-clamp measurements (data not shown).

Figure 1:
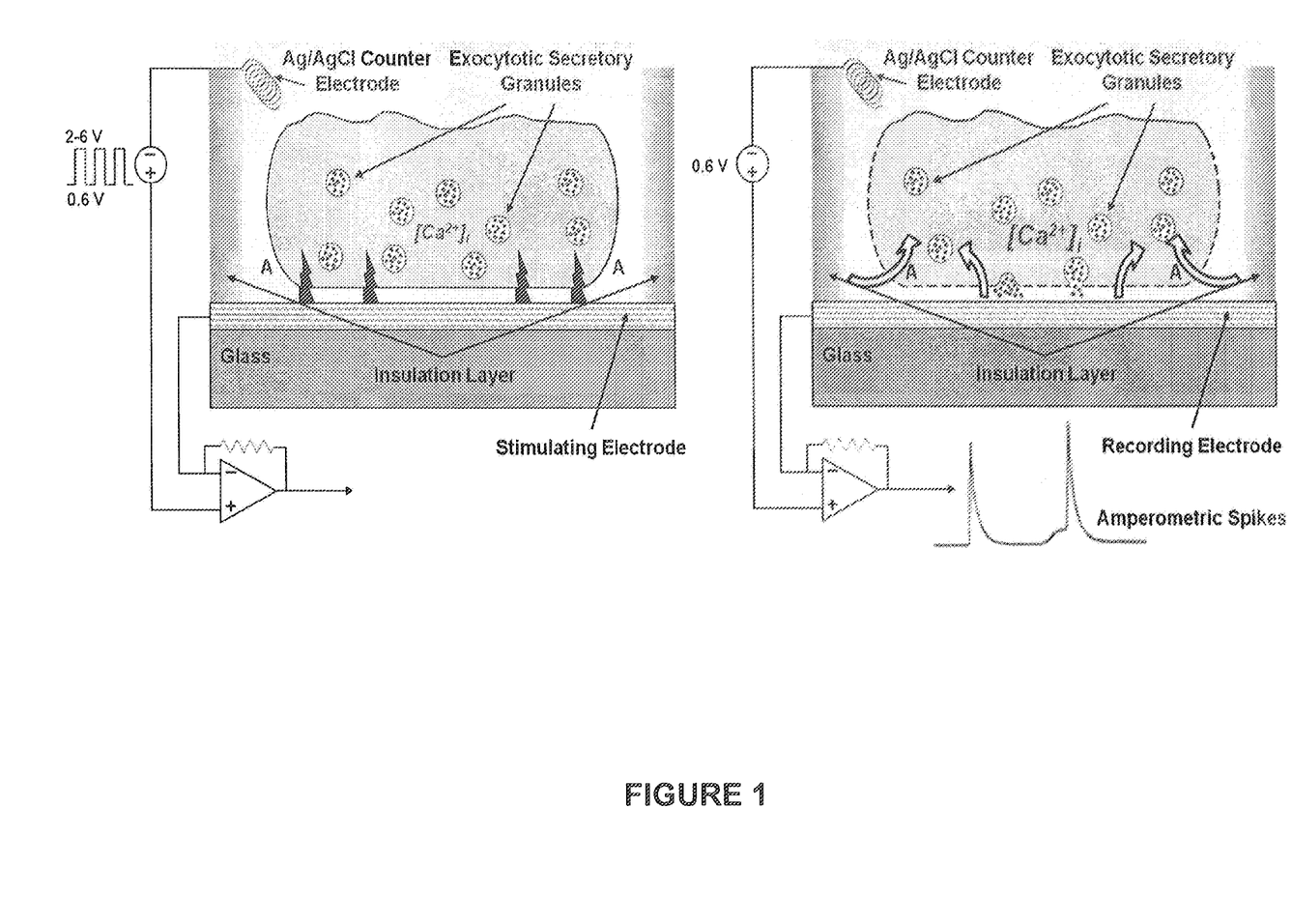
Figure 4A:
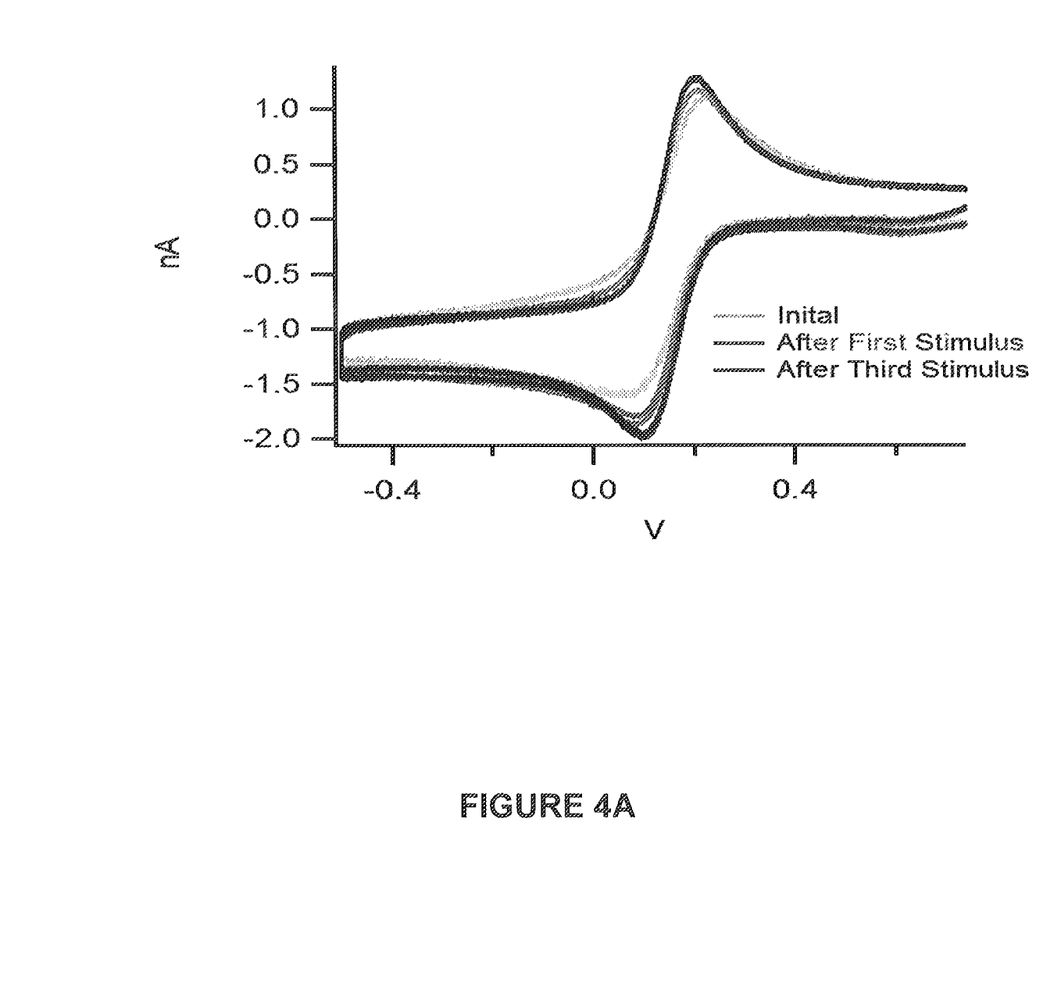
FIGS. 4A and 4B. Voltage pulses sufficient to induce electroporation do not degrade the electrochemical electrode. A. Cyclic voltammograms were acquired at 1 V/s for a 1 mM ferricyanide solution in 0.1 M KCl, pH3. The DLC:N electrode was 20 µm in diameter. In between CVs the solution was exchanged to a normal extracellular solution and voltage pulses (+10 V for 0.2 ms) were applied. B. Cyclic voltammograms were acquired at 1 V/s for a 1 mM ferricyanide solution in 0.1 M KCl, pH3. The Au electrode was 20 μm in diameter. In between CVs the solution was exchanged to a normal extracellular solution and voltage pulses (+10 V for 0.2 ms) were applied.
Figure 4B:
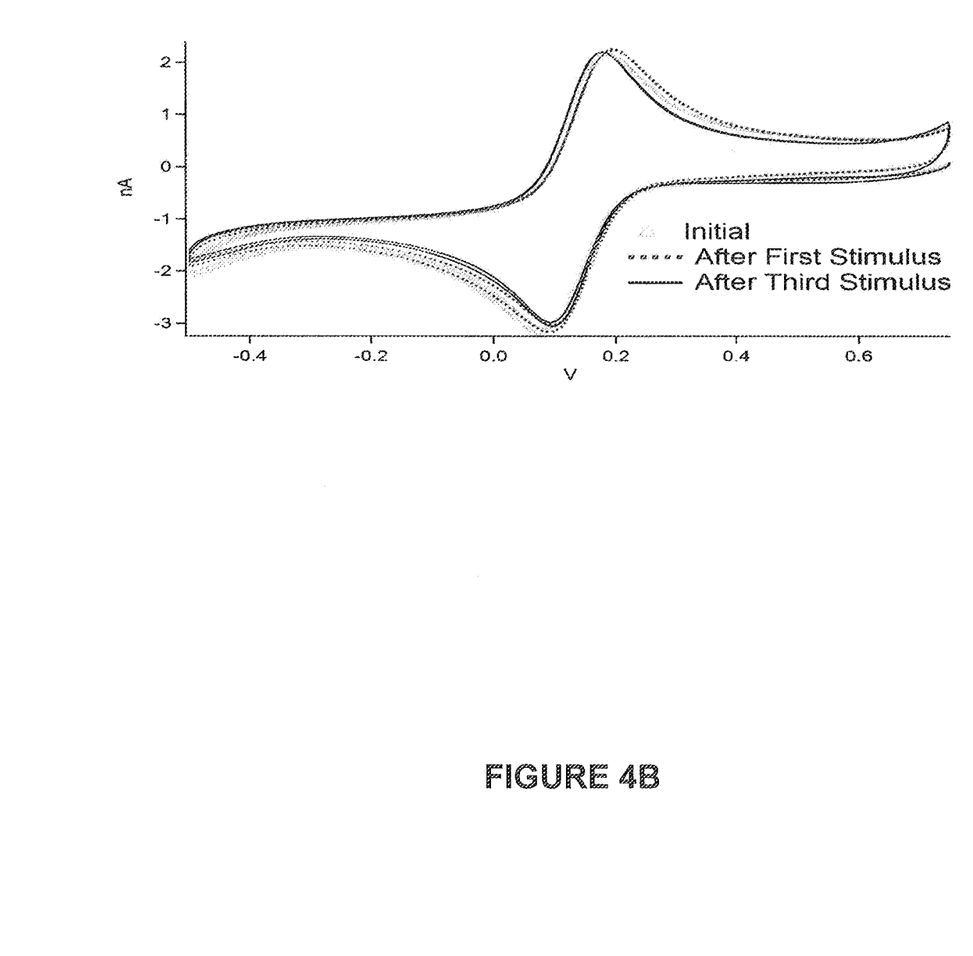

The experiments depicted in FIGS. 1 and 2 demonstrate that the electrochemical electrode can record amperometric spikes with typical features following a voltage pulse, nevertheless, it is possible that voltage pulses will alter the sensitivity or noise of the electrodes. Our preliminary experiments indicate no change in noise by brief (sub ms) pulses to +10V (data not shown). We measured cyclic voltammograms using the test analyte ferricyanide before and after voltage pulses to test for changes in $\Delta E_p$ indicative of changes in electron-transfer kinetics. FIG. 4 is a sample experiment of this type demonstrating little effect of a 0.2 ms pulse to +10 V on the CV.

Optimization of Stimulus Protocol.

The electrical stimulation protocol consists of one or more voltage step(s) from the normal potential used for amperometry (~0.6V) to a test potential (+3 to +10 V) for a duration ranging from 0.1 or 0.2 ms. Bubbles can form on the surface of the electrode if the voltage pulse is too long, so we visually monitored the electrodes while developing stimulus protocols. On the occasion when we did observe a bubble, the cell was displaced from the electrode surface so we could not record exocytosis. Our experience is that milder stimuli lead to exocytosis that terminates in a few seconds whereas a second pulse leads to another burst of release. On the other hand, stronger stimuli lead to release lasting for minutes. Transient electropermeabilization will leave the cell more intact to allow probing the cell over prolonged intervals and is appropriate for introducing exogenous substances into the cell whereas prolonged permeabilization is necessary when the goal is to clamp the intracellular concentration of ions to that of the bath solution. Pore resealing times have been shown to correlate with the strength of the electroporation stimulus [12]. We found that trains of voltage pulses of 5-8 V of 0.1-0.5 ms duration can reliably elicit exocytosis lasting for tens of seconds.

While the invention has been described in connection with specific embodiments thereof, it will be understood that the inventive device is capable of further modifications. This patent application is intended to cover any variations, uses, or adaptations of the invention following, in general, the principles of the invention and including such departures from the present disclosure as come within known or customary practice within the art to which the invention pertains and as may be applied to the essential features herein before set forth.

EXAMPLES

The disclosed exemplary embodiments are merely representative of certain aspects the invention, which may be embodied in various forms. Thus, the exemplary structural, procedural, and functional details disclosed herein are not to be interpreted as limiting.

Example 1

Construction of and Use of Microchip

A semi-transparent Au film was sputter deposited on top of an adhesion promoting Ti film using an RF magnetron sputtering system. The Au/Ti film was patterned using photolithography and wet etching into conductive traces with connection pads arranged around the circumference of the chip to facilitate external connections. A thick photoresist SU-8 2025 was spin-coated on the patterned Au substrate to fabricate working electrodes and cell docking sites as well as to insulate non-active areas of the conductive film. A PDMS gasket with a slit in the middle was fabricated and air plasma-sealed to the device in order to confine the drop of solution containing cells to the part on the device where the working electrodes are located. Gold and diamond-like-carbon (DLC) microelectrodes were found to be effective at eliciting exocytosis from bovine adrenal chromaffin cells via electroporation. The potentiostat used was modified by adding a diode network to allow it to pass large transient currents to enable electroporation, yet record pA amperometric currents with low noise. Parameters of the voltage pulse protocol that were applied to electropermeabilize the cells and optimized for maximum efficiency included voltage applied, pulse-width, and number of pulses. While applying the voltage pulse, the surface of the electrode was visually monitored to detect formation of any kind of bubbles in the solution. When the microelectrode passed current, voltage drop occurred in the electrolytic solution and this voltage gradient surrounding the cell led to an altered potential across regions of the membrane that are orthogonal to the electric field lines. The electric field being the strongest near the cell-electrode interface at the bottom of the cell of interest, effective permeabilization occurred at the membrane near the electrode. Successful electroporation of the plasma membrane was specifically demonstrated by cell uptake of trypan blue. The fluorescent $Ca^{2+}$-indicator Fura-4F was used to measure changes in intracellular $Ca^{2+}$ concentration caused by electropermeabilization.

Example 2

Electroporation Induced Exocytosis

Figure 5:
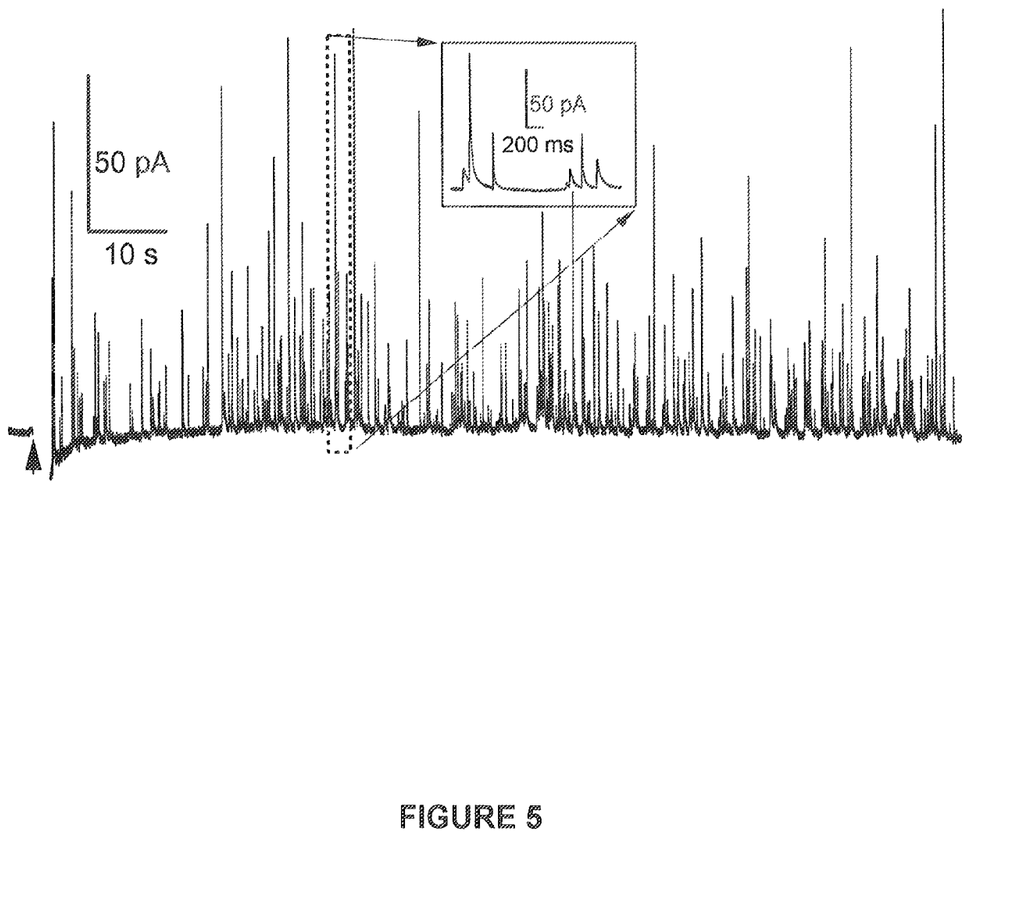

Trains of voltage pulses, 5-7 V in amplitude and 0.1-0.2 ms in duration, reliably triggered exocytosis in single chromaffin cells. The bath solution contained 135 mM NaCl and 2 mM $CaCl_2$. Recordings from such stimulation experiments consisted of trains of individual spikes of amperometric current, tens of pA in amplitude and tens of ms in duration (FIG. 5). Each spike of current serves as a "signature" of exocytosis of an individual secretory granule. Sub-threshold or milder stimulations were found to induce momentary bursts of spike activity, presumably due to transient electropermeabilization, while the standardized protocol led to reliable prolonged exocytosis. Both of these stimuli types can be useful for studies of exocytosis—whereas transient electropermeabilization could leave the cell more intact to allow probing the cell over prolonged intervals, prolonged permeabilization would be necessary to study the dependency of exocytosis on external factors like changing concentrations of a molecule of interest in the external solution.

Individual device electrodes could be cleaned and re-used for multiple (~5) times and cyclic voltammetry tests also confirmed that voltage pulses did not degrade the sensitivity of the electrochemical electrodes.

On electropermeabilization of cells, uptake of trypan blue stain was observed, verifying that the plasma membrane was permeabilized. Modest increases in intracellular $Ca^{2+}$ concentration measured using a fluorescent $Ca^{2+}$ indicator were also observed following electropermeabilization.

Example 3

Stimulation of Exocytosis by Electroporation of Chloride Ion

Figure 6:
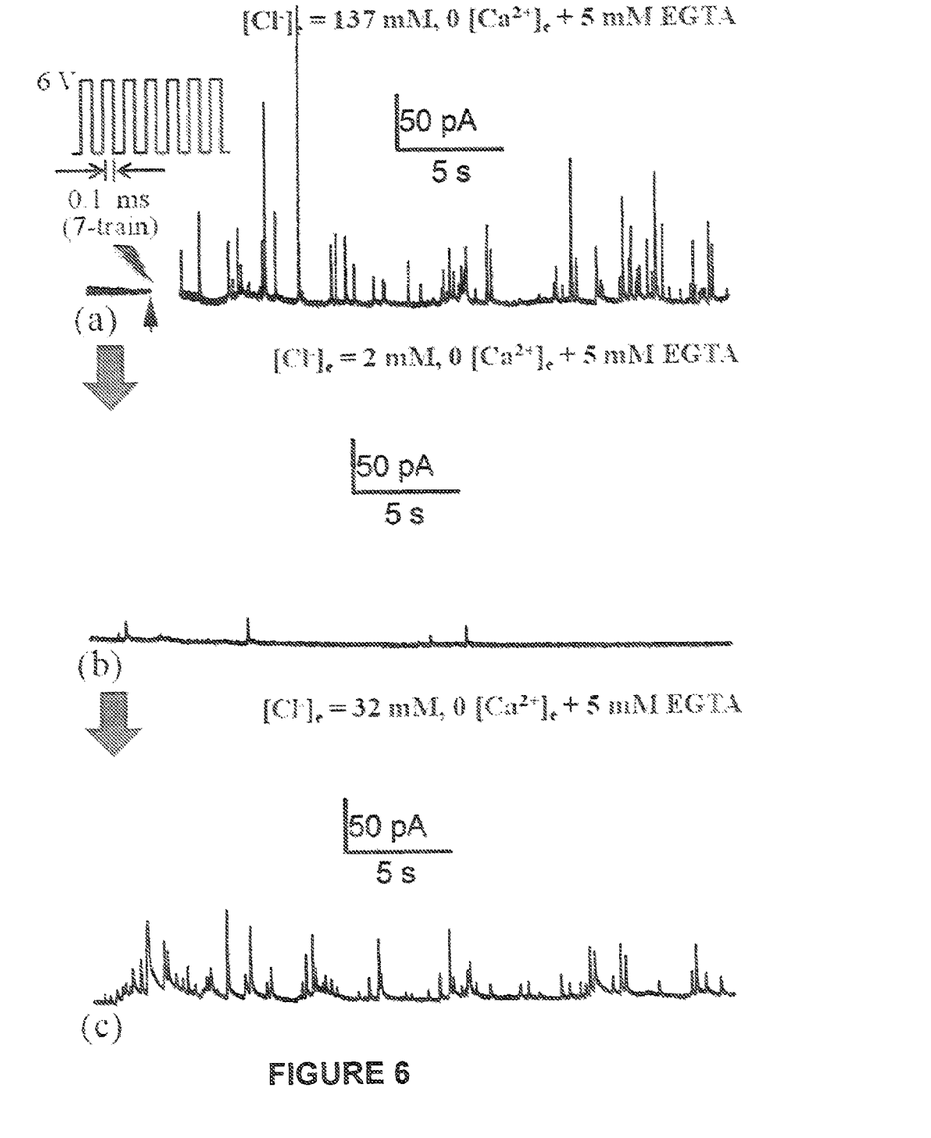

It is well established that exocytosis in excitable cells such as chromaffin cells is triggered by the influx of $Ca^{2+}$. Since the concentration of $Ca^{2+}$ in the extracellular solution ($[Ca^{2+}]_e$) is usually much higher than the intracellular solution, electropermeabilization can be expected to trigger exocytosis by allowing $Ca^{2+}$ entry into the cell. We were surprised to observe, however, that electropermeabilization leads to a vigorous rate of exocytosis even when the extracellular solution contained no added $Ca^{2+}$ plus the addition of 5 mM EGTA (ethylene glycol tetraacetic acid) to thoroughly chelate any residual $Ca^{2+}$ in the water (FIG. 6A). In contrast, we found that 32 mM $[Cl^-]_e$ was sufficient to lead to robust exocytosis following electropermeabilization of the cell membrane in this experiment (FIG. 6). As seen in FIG. 6, the secretion frequency was high when the cell was permeabilized in the first high-$[Cl^-]_e$ solution, fell dramatically when exposed to a second lower-$[Cl^-]_e$ solution, and then increased again when exposed to a higher-$[Cl^-]_e$ solution. All three solutions contained no added $Ca^{2+}$ plus 5 mM EGTA and $[Cl^-]_e$ was varied upon substitution with the anion glutamic acid while maintaining a pH of 7.2. Electropermeabilization in the presence of glutamic acid alone did not yield exocytosis.

We quantified the spike frequency in different $[Cl^-]_e$ solutions as summarized in Table 1. In the first experiment, data were pooled from 5 electropermeabilized cells that were exposed to solutions with $Cl^-$-concentrations in the following sequence (in mM): 135→0→30. Note that the spike frequency is highest with the first solution, dips to almost zero in the second solution and shows an 18-fold increase as high-$Cl^-$ is re-introduced into the external solution. The second case deals with bracketed experiments (n=5) where $[Cl^-]_e$ is varied in the following order (in mM): 135→0→135. Again, the frequency is highest in the initial solution, near-zero in the solution with 0 $Cl^-$ and increases by 6 times when $Cl^-$ is brought back up to the initial concentration. It can be noted that the lower frequency in the third solution compared to the first solution can be attributed to a run-down of exocytosis that is commonly observed for many types of stimuli that lead to high rates of exocytosis.

TABLE 1

| $[Cl^-]_e$ in solution | # of | Spike Frequency (Spikes/s) |
|---|---|---|
| 135 mM→0 mM→30 | 5 | 3.80→0.10→1.77 |
| 135 mM→0 mM→135 | 5 | 7.82→0.17→1.06 |

Inspection of the spikes obtained from these experiments indicates that they have the characteristic fast rise and exponential fall expected for single-vesicle release events (quantal exocytosis). Therefore, spikes induced by electropermeabilization in $Cl^-$-containing solutions appear to have similar properties as those elicited using other more common methods such as cell depolarization. To quantify this, we analyzed 771 spikes from 9 individual cells stimulated in solutions with a range of $[Cl^-]_e$ using the software of Segura et al. [15]. The mean±standard error of the pooled data for the spike parameters were as follows: peak spike current ($I_{max}$), time-to-peak ($t_p$), spike charge (Q) and spike duration (interval where the amperometric current exceeds 50% of the peak value, $t_{1/2}$) were 64.1±1.4 pA, 11.0±0.1 ms, 2.2±0.1 pC and 31.4±0.4 ms respectively. The values are comparable to those found using different stimulus methods that depend on $Ca^{2+}$ influx [16, 17, 18, 19]. Thus it can be inferred that chloride-stimulated, electropermeabilization-induced catecholamine release likely occurs via bona-fide exocytosis of normal secretory granules.

Having illustrated and described the principles of the present invention, it should be apparent to persons skilled in the art that the invention can be modified in arrangement and detail without departing from such principles. Although the materials and methods of this invention have been described in terms of various embodiments and illustrative examples, it will be apparent to those of skill in the art that variations can be applied to the materials and methods described herein without departing from the concept, spirit and scope of the invention. All such similar substitutes and modifications apparent to those skilled in the art are deemed to be within the spirit, scope and concept of the invention as defined by the appended claims.

REFERENCES

1. Chen, P., et al., *Amperometric detection of quantal catecholamine secretion from individual cells on micromachined silicon chips*. Anal Chem, 2003. 75(3): p. 518-24.
2. Chen, X., et al., *Controlled on-chip stimulation of quantal catecholamine release from chromaffin cells using photolysis of caged Ca2+ on transparent indium-tin-oxide microchip electrodes*. Lab Chip, 2008. 8(1): p. 161-9.
3. Sun, X. and K. D. Gillis, *On-chip amperometric measurement of quantal catecholamine release using transparent indium tin oxide electrodes*. Anal Chem, 2006. 78(8): p. 2521-5.
4. Spegel, C., et al., *On-chip determination of dopamine exocytosis using mercaptopropionic acid modified microelectrodes*. Electroanalysis, 2007. 19: p. 263-271.
5. Spegel, C., et al., *Fully automated microchip system for the detection of quantal exocytosis from single and small ensembles of cells*. Lab Chip, 2008. 8(2): p. 323-9.
6. Fromherz, P. and A. Stett, *Silicon-Neuron Junction: Capacitive Stimulation of an Individual Neuron on a Silicon Chip*. Physical Review Letters, 1995. 75(8): p. 1670-1673.
7. Zeck, G. and P. Fromherz, *Noninvasive neuroelectronic interfacing with synaptically connected snail neurons immobilized on a semiconductor chip*. Proc Natl Acad Sci USA, 2001. 98(18): p. 10457-62.
8. Wang, M., et al., *Single-cell electroporation*. Anal Bioanal Chem, 2010. 397(8): p. 3235-48.
9. Hay, J. C. and T. F. Martin, *Resolution of regulated secretion into sequential MgATP-dependent and calcium-dependent stages mediated by distinct cytosolic proteins*. J Cell Biol, 1992. 119(1): p. 139-51.

10. Cahill, P. S. and R. M. Wightman, *Simultaneous amperometric measurement of ascorbate and catecholamine secretion from individual bovine adrenal medullary cells.* Anal Chem, 1995. 67(15): p. 2599-605.
11. Olofsson, J., et al., *Single-cell electroporation.* Curr Opin Biotechnol, 2003. 14(1): p. 29-34.
12. Ryttsen, F., et al., *Characterization of single-cell electroporation by using patch-clamp and fluorescence microscopy.* Biophys J, 2000. 79(4): p. 1993-2001.
13. Lambie, B. A., et al., *Experimentally determining the iR drop in solution at carbon fiber microelectrodes with current interruption and application to single-cell electroporation.* Anal Chem, 2007. 79(10): p. 3771-8.
14. Barbour, B. and P. Isope, *Combining loose cell-attached stimulation and recording.* J Neurosci Methods, 2000. 103(2): p. 199-208.
15. Segura, F., et al., *Automatic analysis for amperometrical recordings of exocytosis.* J Neurosci Methods, 2000. 103(2): p. 151-6.
16. Yang, Y., et al., *Phosphomimetic mutation of Ser-187 of SNAP-25 increases both syntaxin binding and highly Ca2+-sensitive exocytosis.* J Gen Physiol, 2007. 129(3): p. 233-44.
17. Elhamdani, A., H. C. Palfrey, and C. R. Artalejo, *Quantal size is dependent on stimulation frequency and calcium entry in calf chromaffin cells.* Neuron, 2001. 31(5): p. 819-30.
18. Wightman, R. M., et al., *Temporally resolved catecholamine spikes correspond to single vesicle release from individual chromaffin cells.* Proc Natl Acad Sci USA, 1991. 88(23): p. 10754-8.
19. Chow, R. H., L. von Ruden, and E. Neher, *Delay in vesicle fusion revealed by electrochemical monitoring of single secretory events in adrenal chromaffin cells.* Nature, 1992. 356(6364): p. 60-3.

What is claimed is:

1. A method for stimulating and measuring exocytosis from a cell, comprising:

applying at least one voltage pulse to a cell that is in the presence of an exogenous inorganic anion and in the absence of exogenous free calcium ions through an electrode on a device to provide a voltage gradient in solution surrounding the cell, said cell residing in a drop of solution such that said cell is adjacent to said electrode, said solution drop comprising said exogenous inorganic anion, prepared without addition of a calcium ion source compound, and being confined to a part on the device where the electrode is located such that said solution drop is sitting on a surface of said electrode, the applied voltage and concentration of said inorganic anion being sufficient to cause a stimulation of said cell; and, recording, through said same electrode while the cell remains adjacent to the electrode, a current signal indicative of a release of an electrochemically active substance from said stimulated cell.

2. The method of claim 1 wherein a 3V to 10V are applied to said electrode in said applying step and a potentiostat records a pico-amp level current through said electrode in said recording step.

3. The method of claim 1, wherein said exogenous anion is at a concentration of at least about 100 millimolar.

4. The method of claim 1, wherein exogenous free calcium ions are absent when said voltage pulse is applied.

5. The method of claim 1, wherein said inorganic anion is selected from the group consisting of bromide, chloride, iodide, and sulfate.

6. The method of claim 5, wherein said inorganic anion is a chloride ion.

7. The method of claim 1, wherein said voltage pulse exhibits a voltage of 5 V to 8 V and a duration of 0.1 ms to 0.5 ms.

8. The method of claim 7, wherein said applying step comprises applying a train of voltage pulses to said cell through said electrode.

* * * * *